(12) United States Patent
Genshaw

(10) Patent No.: US 7,212,925 B2
(45) Date of Patent: May 1, 2007

(54) CALIBRATION DATA ENTRY SYSTEM FOR A TEST INSTRUMENT

(75) Inventor: Marvin A. Genshaw, Elkhart, IN (US)

(73) Assignee: Bayer Healthcare LLC., Tarrytown, NY (US)

( * ) Notice: Subject to any disclaimer, the term of this patent is extended or adjusted under 35 U.S.C. 154(b) by 85 days.

(21) Appl. No.: 10/750,270

(22) Filed: Jan. 2, 2004

(65) Prior Publication Data

US 2004/0142483 A1 Jul. 22, 2004

Related U.S. Application Data

(60) Provisional application No. 60/440,860, filed on Jan. 21, 2003.

(51) Int. Cl.
*G06F 13/14* (2006.01)

(52) U.S. Cl. .......................... 702/23; 702/30; 702/179; 702/183

(58) Field of Classification Search .................. 702/30, 702/85, 100, 104, 179, 183, 23, 189; 436/50; 600/316; 700/218
See application file for complete search history.

(56) References Cited

U.S. PATENT DOCUMENTS

| | | | | |
|---|---|---|---|---|
| 5,174,963 | A | 12/1992 | Fuller et al. | 422/82.05 |
| 5,507,288 | A | 4/1996 | Bocker et al. | 600/322 |
| 5,695,623 | A | 12/1997 | Michel et al. | 204/403.05 |
| 5,856,195 | A * | 1/1999 | Charlton et al. | 436/50 |
| 5,989,917 | A | 11/1999 | McAleer et al. | 436/46 |
| 6,106,780 | A * | 8/2000 | Douglas et al. | 422/58 |
| 6,295,506 | B1 | 9/2001 | Heinonen et al. | 702/104 |
| 6,560,471 | B1 * | 5/2003 | Heller et al. | 600/347 |
| 6,750,962 | B2 * | 6/2004 | Douglas et al. | 356/246 |
| 7,041,468 | B2 * | 5/2006 | Drucker et al. | 435/14 |
| 2002/0082797 | A1 | 6/2002 | Deweese et al. | 702/122 |

FOREIGN PATENT DOCUMENTS

| EP | 0 840 122 A2 | 5/1998 |
|---|---|---|
| EP | 1 258 728 A2 | 11/2002 |

* cited by examiner

*Primary Examiner*—Marc S. Hoff
*Assistant Examiner*—Felix Suarez
(74) *Attorney, Agent, or Firm*—Jenkens & Gilchrist

(57) ABSTRACT

A test device for determining the analyte concentration in body fluid. The test device has a memory in which calibration adjustments corresponding to calibration numbers are stored. The test device is adapted to receive a test sensor for collecting a sample. The test sensor contains a reagent adapted to produce a reaction indicative of the analyte concentration in the sample and the test sensor has an associated calibration number of a plurality of digits. The test device comprises a measuring unit, a single calibration input element, a user display, and a processor. The measuring unit measures the reaction of the reagent and the analyte and generates a signal indicative of the measured reaction. The single calibration input element permits a user to input the calibration number, one digit at a time, associated with the test sensor. The processor is adapted to determine the analyte concentration. The user display shows available digits to be selected by a user inputting the calibration number and displays the determined analyte concentration.

46 Claims, 4 Drawing Sheets

CALIBRATION DATA ENTRY SYSTEM FOR A TEST INSTRUMENT

CROSS-REFERENCE TO RELATED APPLICATIONS

This application claims the benefit of the U.S. Provisional Application 60/440,860, filed on Jan. 21, 2003 and entitled "Calibration Data Entry System for a Test Instrument", which is hereby incorporated by reference in its entirety.

FIELD OF THE INVENTION

The present invention relates generally to self-monitoring systems and, more particularly, to the entry of calibration data into a test instrument.

BACKGROUND OF THE INVENTION

Those who have irregular blood-glucose concentration levels are often medically required to self-monitor their blood-glucose concentration level. An irregular blood-glucose level can be brought on by a variety of reasons including illness, such as diabetes. The purpose of monitoring the blood-glucose level is to determine the concentration level and then to take corrective action, based upon whether the level is too high or too low, to bring the level back within a normal range. The failure to take corrective action can have serious medical implications.

Beyond the above-describe blood-glucose concentration level monitoring, self-testing systems are used for determining the presence or concentration of other analytes in body fluid such as, for example, cholesterol, alcohol, and hemoglobin in blood or chemical substances in saliva. Beyond self-testing situations, portable test devices are also used to test for various type of chemicals in water and soil.

One method of monitoring a person's blood glucose level is with a portable, hand-held blood glucose test device. A prior art blood-glucose test device 6 is illustrated in FIG. 1. The portable nature of these devices 6 enables the users to conveniently test their blood glucose-levels wherever the users may be. The test device 6 receives a test sensor 7 for harvesting the blood for analysis. The test sensor 7—one of which is required for each test—contains a reaction area including a regent for producing a measurable reaction with the glucose indicative of the blood-glucose concentration level. The test sensor harvests the blood, either prior to or subsequent to insertion into the testing device, for reaction with the reagent stored within.

The device 6 contains a switch 8*a* to activate the device 6 and a display 9 to display the blood-glucose analysis results. Alternatively, the device 6 is automatically activated upon receipt of the test sensor 7. In order to check the blood glucose level, a drop of blood is obtained from, for example, a lanced fingertip. The blood is harvested using the test sensor 7. The test sensor 7, which is inserted into a test device 6, is brought into contact with the blood drop. The test sensor 7 moves the blood to the inside of itself via, for example, capillary action. Alternatively, the a blood sample is harvested with the test sensor 7 prior to inserting the test sensor 7 into the test device. The blood sample now within the test sensor 7 mixed with the reagent causing a reaction between the reagent and the glucose in the blood sample. The test device 6, then measures the reaction to determine the concentration of glucose in the blood. Once the results of the test are displayed on the display 9 of the test device 6, the test sensor 7 is discarded. Each new test requires a new test sensor 7. There are different types of test sensors for use with different types of test devices. Electrochemical or optical (e.g., colorimetric) assays are two types of testing used to measure blood-glucose concentration levels.

During the manufacture of the reagents used within the test sensors or during the manufacture of the test sensors themselves, manufacturing variations occur from batch of test sensors to batch, also referred to as a "lot," of test sensors that impact the performance of the test sensors or that impact the performance of the reagent in the test sensors. For electrochemical sensors, such variations within normal manufacturing tolerances include the size of the electrodes, the amount of reagent deposited within the sensor, the reactivity of the reagent (e.g., rate of dissolution and enzyme activity), and other sensor geometry variations. For optical sensors, manufacturing variations can include the reflectance of the sensor backing, absorbance level of the reagent, the amount of reagent deposited within the sensor, and transmittance of the sensor optics.

To correct for these variations, every package of test sensors is given a calibration number that corresponds to calibration adjustments stored in the testing device. The calibration adjustments inform the test device of how to adjust the obtained measurement for each particular batch of test sensors. Depending on the test device, there may be over 64 calibration algorithms and associated adjustments stored in the test device. Prior to each test, the user inputs the particular calibration number that corresponds to the correct calibration adjustment for the particular batch of test sensors currently being used for the analysis.

In many prior art devices, the test device 6 has a plurality of buttons 8*b*–*e* (FIG. 1) for inputting the calibration number into the test device. An increased number of buttons in the test device adds to the overall cost of the device and adds to the time to manufacture the device.

Other prior art test devices utilize a reading means such as a bar code scanner for reading the calibration number that has been bar coded on the package of test sensors. Other test sensors may be provided with a resistor that informs the test device, which must include an ohm meter for reading the resistor, of the calibration number. Both of these reading means add to the overall cost of the device. Further, the bar coded label can become torn or otherwise destroyed during shipping, making it unreadable, and the resistor can be damaged during shipping.

Other test devices utilize one button, which when pressed, causes the test device to scroll through all of the calibration numbers stored in the test device. While this minimizes the cost of production and the likelihood of breakdown, it is time consuming for the consumer to have to scroll through a plurality of numbers stored in the device, which, in turn, further increases the overall testing time.

SUMMARY OF THE INVENTION

A test device for determining the concentration of an analyte in body fluid is disclosed according to one embodiment of the present invention. The test device has a memory in which a plurality of calibration adjustments corresponding to a plurality of calibration numbers are stored. The test device is adapted to receive a test sensor for collecting a sample, wherein the test sensor contains a reagent adapted to produce a reaction indicative of the concentration of the analyte in the sample and the test sensor has an associated calibration number of a plurality of digits. The test device comprises a measuring unit, a single calibration input element, a user display, and a processor electronically coupled to the single calibration input element, the measuring unit, and the user display. The a measuring unit measures the reaction of the reagent and the analyte and generates a signal indicative of the measured reaction. The single calibration input element permits a user to input the calibration number, one digit at a time, associated with the test sensor. The processor is adapted to determine the concentration of the analyte in the sample in response to receiving the inputted calibration number and receiving the signal indicative of the measured reaction from the measuring unit. The user display displays digits to be selected from by a user inputting the calibration number and displays the determined concentration of the analyte in the sample.

The above summary of the present invention is not intended to represent each embodiment, or every aspect, of the present invention. Additional features and benefits of the present invention will become apparent from the detail description, figures, and claims set forth below.

Figure 1:
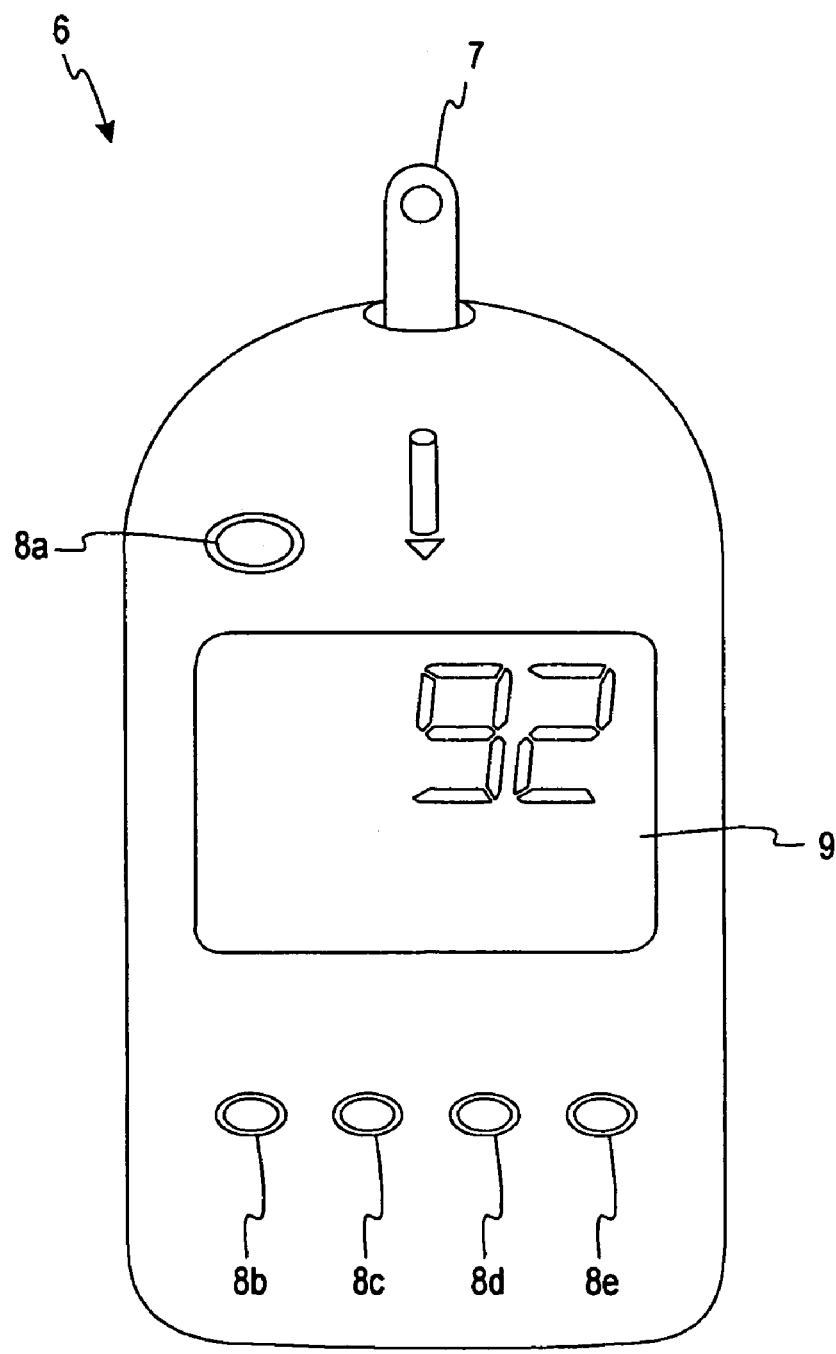
FIG. 1 is a top view of a prior art blood glucose test device.

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents and alternatives falling within the spirit and scope of the invention as defined by the appended claims.

DESCRIPTION OF THE ILLUSTRATED EMBODIMENTS

Figure 2:
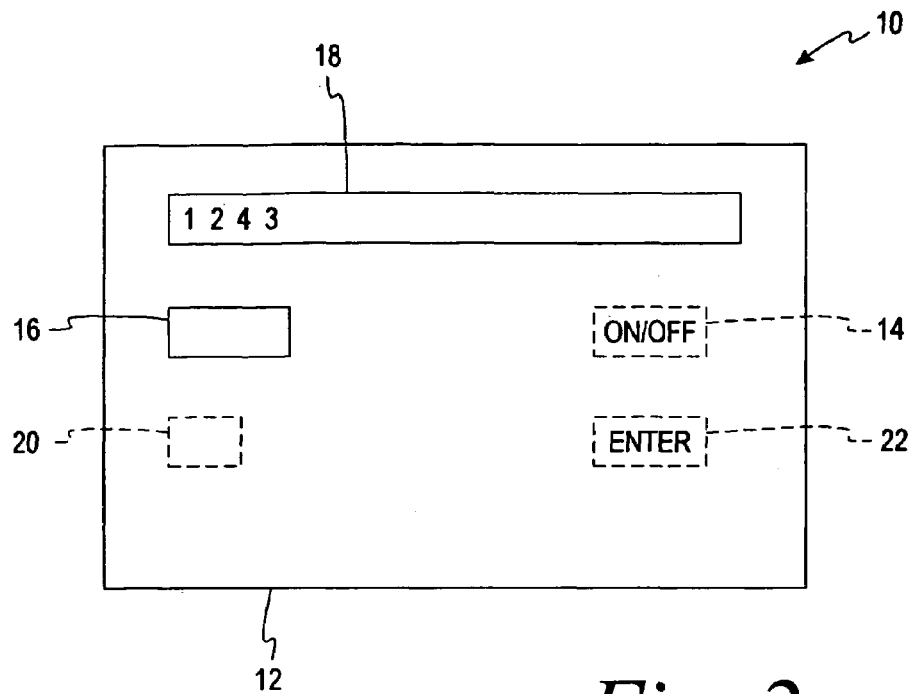
FIG. 2 is a top view of a test device according to one embodiment of the present invention.

Referring now to FIG. 2, there is shown the a test device 10 for determining a user's blood-glucose concentration level according to one embodiment of the present invention. While the following discussion describes determining the concentration of glucose in blood, it is understood that the present invention may be employed in determining the concentration of other analytes in other types of samples.

The test device 10 includes a housing 12, an optional power button 14, a single calibration input element or button 16, a display panel 18, an optional indicating mechanism 20, and an optional end/enter input element or button 22. The power button 14 is used to turn the test device 10 on and off. Alternatively, the test device 10 is automatically activates upon receipt of a test sensor. Alternatively, an initial activation (e.g., depression) of the calibration button 16 activates the test device 10. The single calibration button 16 is used to enter calibration numbers into the test device 10. The display panel 18 displays the numbers that the user enters via the calibration button 16. The optional indicating mechanism 20 (e.g., an LED) is used to alert the user to an alarm condition, such as an abnormal reading, a glucose reading that is too high or too low, or another problem with the test device 10. In an alternative embodiment, there is no an indicating mechanism 20, and the display panel 18 is used to alert the user to the alarm condition. The optional enter button 22 is used to submit the calibration number—that is shown on the display panel 18—to the test device 10 once the numbers have been properly entered by the user. Alternatively, the calibration number entered by the user via the calibration button 16 is accepted by the test device 10 after a period of inactivity.

Figure 3:
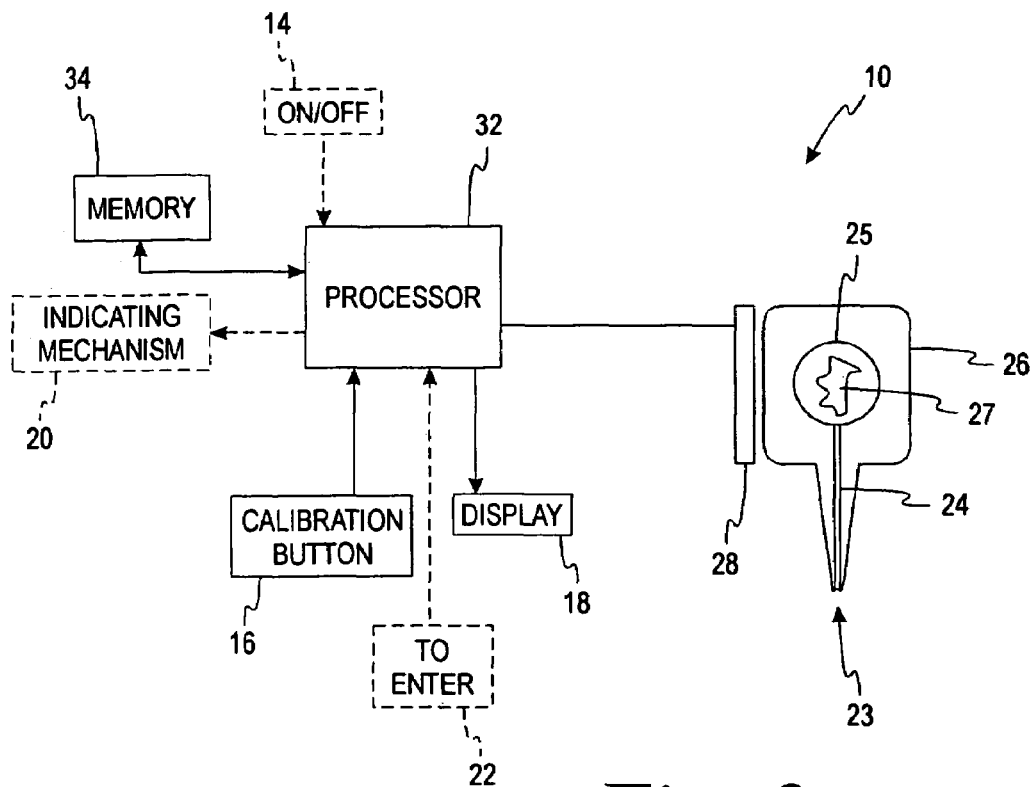
FIG. 3 is a functional block diagram of the test device of FIG. 2.

Referring to FIG. 3, the internal components of the test device 10 will be described. The test device 10 includes a measuring unit 28 that receives a fluid collection apparatus or test sensor 26. In embodiments where electrochemical testing is implemented, the measuring unit 28 comprises an amp meter for measuring current. In embodiments where colorimetric testing is implemented, the measuring unit comprises a spectrograph, a photometric measuring unit, or other optical measuring unit. The test sensor 26 includes a reagent 27 that reacts with a blood sample creating a measurable reaction indicative of the concentration of glucose in the blood sample.

The type of regent implemented in the test device 10 depends on the type of measuring used. For example, in calorimetric testing, the reagent reacts with the glucose in a blood sample causing a calorimetric reaction indicative of the glucose concentration level. A photometric measuring unit or other optical device reads the degree of color change. Colorimetric testing is described in detail in U.S. Pat. No. 6,181,417 B1 (entitled "Photometric Readhead with Light Shaping Plate"), U.S. Pat. No. 5,518,689 (entitled "Diffuse Light Reflectance Readhead"), and U.S. Pat. No. 5,611,999 (entitled "Diffuse Light Reflectance Readhead"), each of which is incorporated herein by reference in its entirety.

Figure 4:
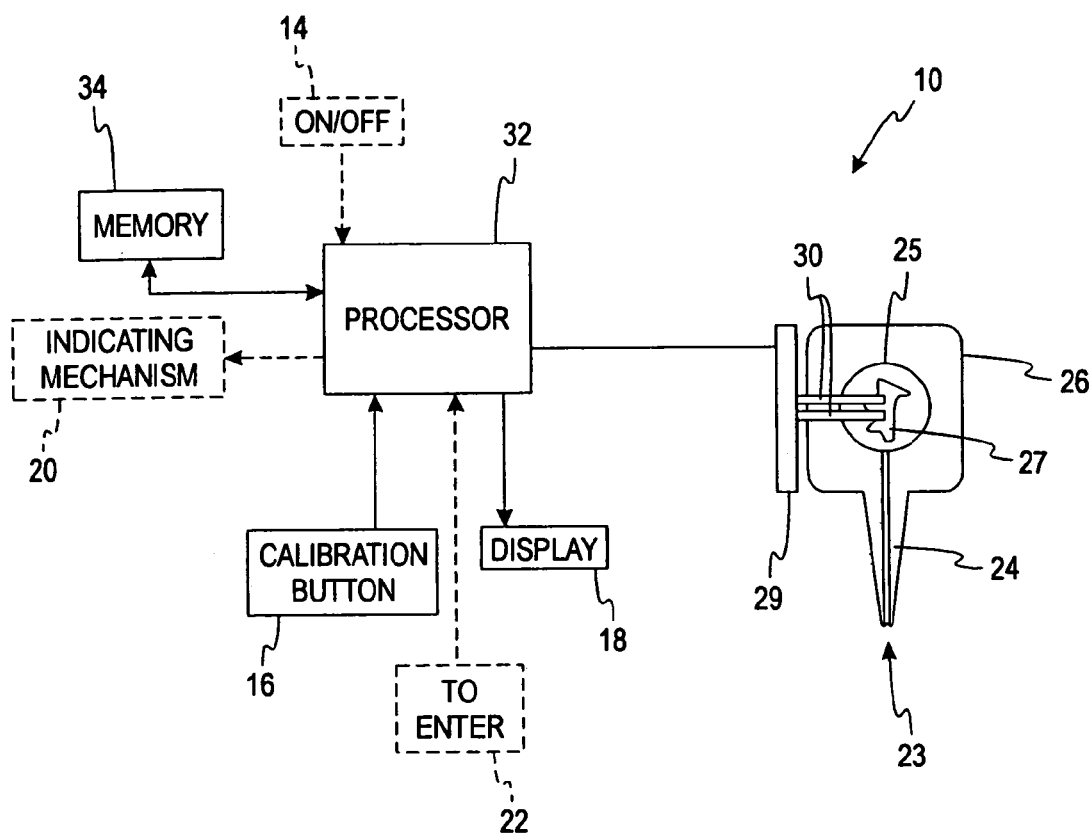
FIG. 4 is a functional block diagram of the test device of FIG. 2 according to an alternative embodiment of the present invention.

Referring also to FIG. 4, a test device 10 having an electrochemical measuring unit 29 is illustrated according to an alternative embodiment of the present invention. In an electrochemical assay, the regent is designed to react with glucose in the blood to create an oxidation current at electrodes 30 which is directly proportional to the concentration of glucose in the user's blood. The current is measured by a measuring unit 29, which is electrically coupled to the electrodes 30. An example of an electrochemical testing system is described in detail by commonly-owned U.S. Pat. No. 5,723,284 entitled "Control Solution and Method for Testing the Performance of an Electrochemical Device for Determining the Concentration of an Analyte in Blood" which is incorporated herein by reference in its entirety.

The test device 10 includes a processor 32 that is electrically coupled to the measuring unit 28, the indicating mechanism 20, and the power button 14. The processor 32 adjusts the output of the measuring unit 28 with calibration adjustments to correct for the manufacturing variations discussed above. In one embodiment of the present invention, the calibration adjustments are stored in a memory 34 of the testing device 10. Alternatively, the calibration adjustments are programmed in the processor 32. The processor 32 is receives input from a user via the calibration button 16 and displays output on the display panel 18.

As discussed in the Background Section, each package of test sensors includes a calibration number for correcting manufacturing variations that occur within normal manufacturing tolerances of the reagent as wells as with the test sensors themselves. For electrochemical sensors, such variations include the size of the electrodes, the amount of reagent deposited on the sensor, the reactivity of the reagent (e.g., rate of dissolution and enzyme activity), and other sensor geometry variations. For optical sensors, manufacturing variations can include the reflectance of the sensor backing, absorbance level of the reagent, the amount of reagent deposited on the sensor, and the reactivity of the reagent and transmittance of the sensor optics.

The processor 32 uses the calibration adjustment for adjusting the measurement obtained by the measuring unit 28 for the particular test sensors 26 used to obtain an accurate reading of the glucose concentration of a sample. The processor 32 stores a plurality of calibration adjustments for programming the test device to correct for the manufacturing variations of reagents. The calibration adjustments have numerical labels—referred to as calibration numbers—that a user inputs to a test device 10 for selecting the appropriate calibration adjustment. The processor 32 associates the calibration number with the calibration adjustment and makes the appropriate adjustments to the output of the measuring unit 28. Each time a lot of reagent is changed—each time the user obtains a new package of test sensors—the user inputs the calibration number associated with that new package so that accurate results are obtained.

The relationship between the blood-glucose concentration level "Y" and the measurement "X" obtained by the measuring unit 28 is governed by a calibration curve. According to one embodiment of the present invention, the calibration curve is linear and is represented by equation (1).

$$Y = k \cdot X + b \quad (1)$$

In equation (1), the slope of the calibration equation is represented by the variable "k" and the y-axis intercept is represented by the variable "b." The adjustments, which are stored in the memory 34 of the test device 10 that correspond to the entered calibration number, represent specific values for the slope (k) and the y-intercept (b) of calibration curve according to one embodiment of the present invention. The memory of the test device 19 has stored therein a look-up table of calibration numbers, a value for the slope for each calibration number, and a value for the y-axis intercept. For example, tests using a test sensor having calibration number 123 associated therewith, the corresponding value for the slope is alpha ($\alpha$) and the corresponding value for the y-intercept is beta ($\beta$). The calibration line for that particular test sensor would be as represented by equation (2).

$$Y = \alpha \cdot X + \beta \quad (2)$$

Thus, the blood-glucose concentration level determined using the particular test sensor would be equal to beta ($\beta$) plus the product of the measurement obtained by the measurement device 20 and alpha ($\alpha$). In other embodiments of the present invention, calibration curves are logarithmic in nature or are exponential in nature. In other embodiments, groups of calibration numbers may be associated with different types of calibration curves. For example, calibration numbers 123–187 may be associated with a linear calibration curve and calibration numbers 212–276 may be associated with an exponential calibration curve.

Figure 5:
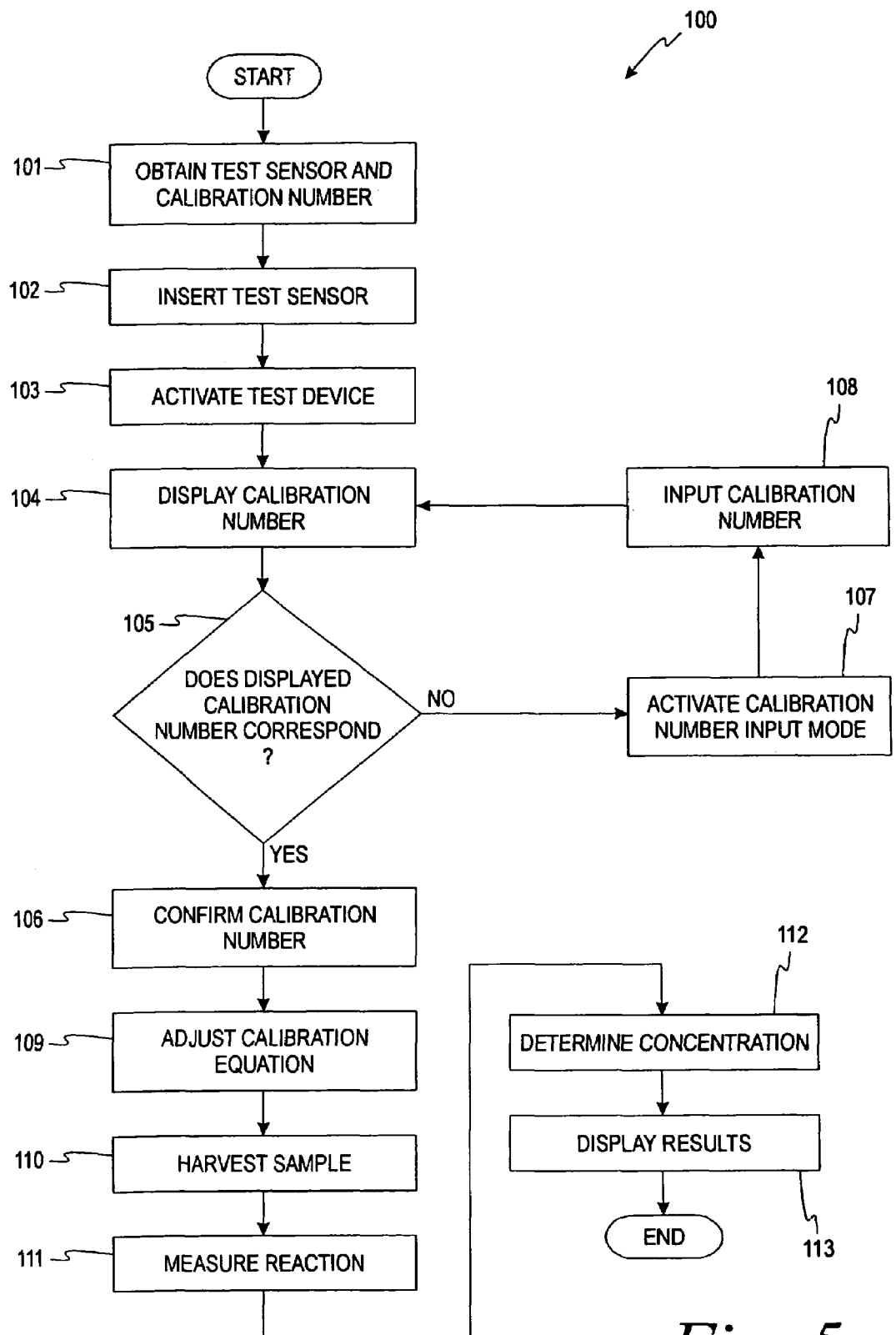
FIG. 5 is a flow chart illustrating the operation of a test device according to one embodiment of the present invention.

Turning now to FIG. 5, a flowchart 100 describing the operation of the test device 10 according to one embodiment of the present invention is illustrated. A user obtains a package of test sensors 26, each including a reagent, that includes a calibration number at step 101. The calibration number informs the processor 32 which calibration adjustment to use to obtain an accurate reading with the obtained package of test sensors. The user inserts a test sensor 26 into the test device 10 at step 102 and then activates the test device 10 by depressing the on/off button 14 at step 103. Alternatively, the test device 10 automatically activates upon detecting an inserted test sensor 26. Alternatively still, the test device 10 is activated by an initial activation or depression of the calibration button, which further reduces the number of buttons of the test device 10.

Upon activation, the test device 10 displays the most recently entered calibration number on the display 18 at step 104. At step 105, the user determines whether the displayed calibration number corresponds to the calibration number corresponding to the test sensor to be used. If the displayed calibration number corresponds to the calibration number of the test sensor to be used, the user confirms as such at step 106 and the user is ready proceed to testing the user's blood-glucose concentration level. The user confirms at step 106 by waiting a predetermined time period, and after the period of inactivity (e.g., a couple or several seconds) the processor accepts the displayed number as the calibration number. Alternatively, in embodiments of the test device 10 implementing the optional enter button 22, the user depresses the enter button 22 to signal to the processor 32 that the displayed calibration number is the correct calibration number. A new calibration number may not have to be input when, for example, the test sensor to be used is part of the same batch of test sensors from which the most-recently used test sensor was obtained. Alternatively, in other embodiments of the present invention, the user is required to enter the calibration number associated with the test sensor currently being used regardless of any previously input calibration number.

If the calibration numbers does not correspond at step 105, the user must input the correct calibration number. The user activates a calibration number input mode of the test device 10 by depressing the calibration button 16 at step 107. The user inputs a multiple-digit (e.g., 2, 3, 4, or 5 digits) calibration number using the single calibration button at step 108. For example, once the calibration button is activated with a single depression of the calibration button 16, the test device 10 is ready to receive the first digit, or field, of a three digit (base number ten) calibration number. The user repeatedly depresses the calibration button 16 to scroll through the ten digits (i.e., 0, 1, 2, 3, 4, 5, 6, 7, 8, and 9), which are displayed on the display 18, to enter the first digit of the three digit calibration number until the user arrives at the correct number. Alternatively, depressing the calibration button 16 and holding the calibration button in a depressed state causes the test device 10 to scroll through the ten digits, with a predetermined time period passing between each digit. The predetermined time period provides sufficient time for the user to view each digit and to react to each displayed digit. Upon arriving at the first digit of the three digit calibration number, the user stops scrolling through digits by deactivating or releasing the single calibration button and after a predetermined amount of time, the processor enters that number as the first digit and then prompts the user for the second digit of three digit calibration number by, for example, moving a cursor on the display 18. The user then enters, via the calibration button 16, the second and third digits of the three digit calibration number in the same manner. Once the complete calibration number (i.e., all of the digits of the calibration number) has been input, the processor 32 displays the calibration number on the display of the test device 10 at step 104. In one embodiment of the present invention, the processor 32 is programmed to expect a calibration number having a predetermined number of digits (e.g., 3) and automatically moves to the next step after all three digits have been entered. Alternatively, the test device 10 accepts calibration numbers of a variety of lengths, and the processor 32 determines that a complete calibration number has been entered after a period of inactivity following the entry of the final digit of the calibration number. Alternatively still, the user indicates that a complete calibration number is entered by depressing the optional enter button 22.

At step 106, the user confirms that the proper calibration number is displayed on the display 18 in the same manner discussed above. The processor 32 then looks up the adjustments to make to the calibration curve in the look-up table stored in memory 34 and makes the appropriate adjustments corresponding to the input calibration to the calibration curve at step 109. If the correct calibration is not displayed, the user repeats the above-described process for entering the correct calibration number.

Next at step 110, the user harvests the user's blood sample with a test sensor received in the testing device. Lancing a user's finger tip is one manner in which a blood sample may be obtained from a user. The blood sample moves to the reaction area of the test sensor, via capillary action, where is mixes with the regent stored in the test sensor for producing a reaction indicative of the concentration of glucose in the blood sample. The measuring unit 28 measures the reaction at step 111. As discussed above, electrochemical assays or colorimetric assays are two types of assays used in analyzing a user's blood-glucose concentration level. The user's blood-glucose concentration level calculated at step 112 with the adjusted calibration curve. The result of the blood-glucose concentration level analysis, including the concentration level, whether the concentration level is above or below a target level, or both, is communicated to the user via the display 18 at step 113.

In the embodiment of present invention discussed in connection with FIG. 5, the calibration number input to the test device 10 is a base ten (10) number. In other alternative embodiments of the present invention, the test device 10 receives calibration numbers of other base number systems including base three (zero through two), base four (zero through three), base five (zero through four), and base six (zero through five). Utilizing systems of lower bases number provides the advantage of limiting the number of digits that a user must scroll through when inputting the calibration number because a user only has to scroll through a few numbers (three, four, five, or six) before arriving at the desired number. For example, when the calibration number is a three-digit base four number (e.g., 032), the user only has to scroll through four numbers for each of the three digits or fields of the calibration number at a maximum. Additionally, if the user scrolls past the desired number, the number of digits the user has to scroll through is less with lower numbered base number systems.

A drawback of calibration numbers of lower numbered based number systems, is that there are less calibration numbers and corresponding calibration curves or equations available to store in the test device 10 when compared to higher numbered base number systems when the same number of digits are used. For example, for a five digit calibration number, the base number three system provides 243 different numbers whereas base number five provides 7776 numbers.

Referring to Table I, the number of available calibration numbers for a plurality of number bases and a plurality of digits is shown.

TABLE I

|  | 1-Digit | 2-Digit | 3-Digit | 4-Digit | 5-Digit |
|---|---|---|---|---|---|
| Base 2 | 2 | 4 | 8 | 16 | 32 |
| Base 3 | 3 | 9 | 27 | 81 | 243 |
| Base 4 | 4 | 16 | 64 | 256 | 1024 |
| Base 5 | 5 | 25 | 125 | 625 | 3125 |
| Base 6 | 6 | 36 | 216 | 1296 | 7776 |
| Base 7 | 7 | 49 | 343 | 2401 | 16807 |
| Base 8 | 8 | 64 | 512 | 4096 | 32768 |
| Base 9 | 9 | 81 | 729 | 6561 | 59049 |
| Base 10 | 10 | 100 | 1000 | 10000 | 100000 |

While increasing the base number permits an increased number of calibration number possibilities, it also increases the numbers that a user must scroll through to arrive at the appropriate number of a particular digit of a calibration number. Likewise, increasing the number of digits will increase the overall time for inputting a calibration number.

Various calibration numbers to be input to the test device 10 may have different numbers of digits according to an alternative embodiment of the present invention. For example, a first batch of test sensors may have a three-digit calibration number associated therewith, and a second batch of test sensors may have a five-digit calibration number therewith. Once the user inputs the calibration number via the calibration button 16, the user depresses the enter button 22 to signal to the processor 32 that the complete calibration number has been input. Alternatively, the processor 32 monitors the time between depressions of the calibration button 16 and accepts the digits entered thus far as the calibration number after the expiration of a predetermined time period following the last depression or release of the calibration button 16. For example, according to one embodiment of the present invention, a three digit calibration number is input to the test device 10 via the calibration button 16. After the user has scrolled to the appropriate number representing the third digit of the calibration number, the user stops depressing the calibration button. The processor 32 times the period of inactively with respect the selection of the last digit. After a predetermined period of inactivity (e.g., three second) the processor 32 accepts the number entered as the calibration number.

According to another embodiment of the present invention, the calibration numbers to be received by the test device 10 are three-digit calibration numbers. For instruments used in the analysis of blood, the display is usually three digits long because three digits are sufficient for displaying results with the acceptable precision. In most situations, increasing the number of digits would not lend to a more meaningful results. And adding to the length of the display increases the overall cost of the testing device. For a three digit calibration number, utilizing number base four allows for a maximum of 64 different calibration numbers, utilizing number base five allows for 125 calibration numbers, and utilizing number base six allows for 216 calibration numbers.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A test device for determining the concentration of an analyte in a sample, the test device having a memory in which a plurality of calibration adjustments corresponding to a plurality of calibration numbers is stored, the test device being adapted to receive a test sensor for collecting the sample, the test sensor containing a reagent adapted to produce a reaction indicative of the analyte concentration in the sample, the test sensor having an associated calibration number of a plurality of digits, the device comprising:
   a measuring unit adapted to measure the reaction of the reagent and the analyte and to generate a signal indicative of the measured reaction;
   a single calibration input element adapted to permit a user to input the calibration number, one digit at a time, associated with the test sensor;
   a processor electronically coupled to the single calibration input element and the measuring unit, the processor being adapted to determine the analyte concentration in the sample in response to receiving the inputted calibration number and receiving the signal indicative of the measured reaction from the measuring unit; and
   a user display electronically coupled to the processor for displaying digits to be selected by a user inputting the calibration number and for displaying the determined analyte concentration in the sample.

2. The device of claim 1 wherein the calibration number includes a first digit and a second digit, the processor being adapted to commence scrolling through a plurality of numbers on the user display, from which the first digit of the calibration number is selected, upon activation of the single calibration input element by the user, the processor being adapted to suspend scrolling through the numbers upon deactivation of the single calibration input element by the user, the processor accepting the number displayed on the user display at the time of the deactivation of the single calibration input element as the first digit of the calibration number.

3. The device of claim 2 wherein the processor accepts the displayed number after a predetermined time period measured from the deactivation of the single calibration input element.

4. The device of claim 2 wherein the processor is adapted to commence scrolling through a plurality of numbers on the user display, from which the second digit of the calibration number is selected, upon activation of the single calibration input element by the user after acceptance by the processor of the first digit of the calibration number, the processor being adapted to suspend scrolling through the numbers upon deactivation of the single calibration input element by the user, the processor accepting the number displayed on the user display at the time of the deactivation of the single calibration input element as the second digit of the calibration number.

5. The device of claim 1 wherein the processor prompts the user, via the display, to input a first digit of the calibration number.

6. The device of claim 5 wherein the processor is adapted to scroll through a plurality of numbers on the user display, from which the first digit of the calibration number is selected, in response to a plurality of activations of the single calibration input element by the user, the processor accepting a displayed number as the first digit of the calibration number after a predetermined time measured from a most-recent activation of the single calibration input element.

7. The device of claim 6 wherein the processor prompts the user, via the display, to input a second digit of the calibration number upon acceptance of the first digit.

8. The device of claim 7 wherein the processor is adapted to scroll through a plurality of numbers on the user display, from which the second digit of the calibration number is selected, in response to a plurality of activations of the single calibration input element by the user, the processor accepting a displayed number as the second digit of the calibration number after a predetermined time measured from the last activation of the single calibration input element.

9. The device of claim 8 wherein the calibration number consists of a predetermined number of digits, the processor automatically adjusting the at least one adjustable parameter of the concentration equation upon receipt of the final digit of the calibration number consisting of a predetermined number of digits.

10. The device of claim 8 further comprising an enter input element for permitting a user to indicate to the processor that all of digits of the calibration number have been entered, the processor automatically adjusting the at least one adjustable parameter of the concentration equation upon activation of the enter input element by the user.

11. The device of claim 1 wherein the calibration number consists of a predetermined number of digits, the processor adjusting the at least one adjustable parameter of the concentration equation according to the stored adjustment corresponding to the input calibration number upon receipt of each of the predetermined number of digits of the calibration number.

12. The device of claim 1 further comprising an enter input element, the processor accepting the inputted calibration number upon receipt user input, via the enter input element, indicating that each of the plurality of digits of the predetermined number have been input.

13. The device of claim 1 wherein the calibration number ranges between two digits and five digits.

14. The device of claim 1 wherein the calibration number has a number base selected from the group consisting of number base three, number base four, number base five, and number base six.

15. The device of claim 1 wherein the processor is adapted to display on the user display a previously entered calibration number upon an initial activation of the single calibration input element.

16. The device of claim 1 wherein the reagent is adapted to produce an optical reaction and the measuring unit is adapted to measure the optical reaction.

17. The device of claim 16 wherein the optical reaction is a colorimetric reaction and the measuring unit is adapted to measure the colorimetric reaction.

18. The device of claim 1 wherein the reagent is adapted to produce an electrochemical reaction and the measuring unit is adapted to measure the electrochemical reaction.

19. The device of claim 1 wherein the sample is blood.

20. The device of claim 1 wherein the analyte is glucose.

21. The device of claim 1 wherein the processor determines the concentration of the analyte in the sample according to a calibration equation having an adjustable parameter, the processor adjusts the adjustable parameter according to the stored adjustment corresponding to the inputted calibration number.

22. A method for entering a multiple-digit calibration number into a test device, the test device having a memory in which a plurality of calibration adjustments corresponding to a plurality of calibration numbers is stored, the test device being adapted to receive a test sensor for collecting a sample, the test sensor containing a reagent adapted to produce a reaction indicative of the analyte concentration in the sample, the test sensor having an associated calibration number, the method comprising the acts of:

prompting a user, via a user display, to enter a digit of the calibration number;

receiving input from the user, via a single calibration input element, indicative of the calibration number, one digit at a time;

measuring the reaction between an analyte in a collected sample and the reagent contained in the test sensor;

determining the analyte concentration in the sample in response to receiving the calibration number from the user and measuring the reaction; and displaying the determined analyte concentration in the sample on the user display.

23. The method of claim 22 wherein receiving input from the user indicative of the calibration number further comprises:

(a) prompting the user to input a particular one of the multiple digits of the calibration number;

(b) scrolling through a plurality of digits, one at a time, from which the particular one of the multiple digits can be selected, on the user display in response to repeated activations of the single calibration input element by the user until a displayed number is displayed on the user display;

(c) accepting the displayed number as the particular one of the multiple-digits of the calibration number; and (d) repeating (a) through (c) until all of the digits of the multiple-digit calibration number have been accepted.

24. The method of claim 23 wherein the accepted digits are accepted by the test device as the calibration number after a predetermined time period of inactivity.

25. The method of claim 23 wherein the accepted digits are accepted by the test device as the calibration number upon receipt of user input, via an enter input element, indicative that all of the digits of the calibration number have been inputted by the user.

26. The method of claim 23 wherein scrolling through a plurality of numbers comprises scrolling through the numbers corresponding to the number base of the calibration number.

27. The method of claim 22 wherein receiving input from the user indicative of the calibration number further comprises:

(a) prompting the user to input a particular one of the multiple digits of the calibration number;

(b) scrolling through a plurality of numbers displayed on the user display, from which the particular one of the multiple digits can be selected, in response to activating the single calibration input element;

(c) suspending the scrolling when a desired number for selection as the particular one of the multiple digits is displayed on the user display in response to deactivating the single calibration input element;

(d) accepting the displayed number as the particular one of the multiple-digits of the calibration number; and (e) repeating (a) through (d) until all of the digits of the multiple-digit calibration number have been accepted.

28. The method of claim 27 wherein the accepted digits are accepted by the test device as the calibration number after a predetermined time period of inactivity.

29. The method of claim 27 wherein the accepted digits are accepted by the test device as the calibration number upon receipt of user input, via an enter input element, indicative that all of the digits of the calibration number have been inputted by the user.

30. The method of claim 27 wherein scrolling through a plurality of numbers comprises scrolling through the numbers corresponding to the number base of the calibration number.

31. The method of claim 22 wherein the multiple-digit calibration ranges between two digits and five digits.

32. The method of claim 22 wherein the calibration number has a number base selected from the group consisting of number base three, number base four, number base five, and number base six.

33. The method of claim 22 wherein measuring comprises measuring an optical reaction.

34. The method of claim 22 wherein measuring comprises measuring a colorimetric reaction.

35. The method of claim 22 wherein measuring comprises measuring an electrochemical reaction.

36. The method of claim 22 wherein the sample is blood.

37. The method of claim 22 wherein the analyte is glucose.

38. The method of claim 22 wherein determining comprises determining the concentration of the analyte in the sample according to a calibration equation having an adjustable parameter and adjusting the adjustable parameter according to the stored adjustment corresponding to the inputted calibration number.

39. A calibration number input system for a test device for measuring the concentration of an analyte in a sample, the test device having a memory in which a concentration equation having at least one adjustable parameter and a plurality of calibration adjustments for the concentration equation corresponding to a plurality of calibration numbers are stored, the input system comprising:

a user display adapted to display information to a user of the test device;

a single calibration input element adapted to permit the user to select digits for inputting a multiple-digit calibration number, one digit at a time; and a processor electronically coupled to the single calibration input element and the user display, the processor prompting the user to input each of the digits of the calibration number, one at a time, the processor receiving the inputted calibration number and adjusting the at least one adjustable parameter of the concentration equation according to the stored adjustment corresponding to the inputted calibration number.

40. The system of claim 39 wherein the processor is adapted to receive a calibration number of a specific number of digits, the processor permitting a user to scroll through an array of numbers being displayed on the user display, one number at a time, such that the next number in the array of numbers to be displayed is displayed in response to each activation of the single calibration input element, each digit of the calibration number being selected from the array of numbers, the processor accepting a displayed number as the particular digit of the calibration number presently being inputted by the user in response to not receiving input from the single calibration input element for a predetermined time period, the processor entering the accepted numbers as the calibration number upon acceptance of a number as a last number of the specific number of digits.

41. The system of claim 39 wherein the processor prompts the user, via the display, to input a first digit of the calibration number upon an initial activation of the single calibration input element.

42. The system of claim 39 wherein the calibration number ranges between two digits and five digits.

43. The system of claim 39 wherein the calibration number has a number base selected from the group consisting of number base three, number base four, number base five, and number base six.

44. The system of claim 39 wherein the numbers in the array of numbers corresponds to the number base of the calibration number.

45. The system of claim 39 wherein the processor is adapted to display on the user display a previously entered calibration number upon an initial activation of the single calibration input element.

46. The system of claim 45 wherein the processor is adapted to enter the displayed previously entered calibration number as the calibration number to be used after a predetermined time period has elapsed measured from the initial activation of the single calibration input element during which the single calibration input element is not activated.

* * * * *